United States Patent
Mundry

(10) Patent No.: US 7,912,249 B2
(45) Date of Patent: Mar. 22, 2011

(54) TOMOGRAPHIC IMAGING

(75) Inventor: Uwe Mundry, Landrum, SC (US)

(73) Assignee: Imaging Sciences International LLC, Hatfield, PA (US)

( * ) Notice: Subject to any disclaimer, the term of this patent is extended or adjusted under 35 U.S.C. 154(b) by 982 days.

(21) Appl. No.: 11/803,069

(22) Filed: May 11, 2007

(65) Prior Publication Data

US 2007/0297663 A1    Dec. 27, 2007

Related U.S. Application Data

(60) Provisional application No. 60/799,584, filed on May 11, 2006.

(51) Int. Cl.
*G06K 9/00*      (2006.01)
(52) U.S. Cl. .................................... 382/109; 382/131
(58) Field of Classification Search ............... 382/109, 382/128, 131, 154; 128/922; 600/416; 703/11; 434/262, 263, 274
See application file for complete search history.

(56) References Cited

U.S. PATENT DOCUMENTS

| | | | | |
|---|---|---|---|---|
| 6,084,989 A | * | 7/2000 | Eppler | 382/293 |
| 6,224,373 B1 | * | 5/2001 | Lee et al. | 433/172 |
| 7,616,800 B2 | * | 11/2009 | Paik et al. | 382/131 |
| 2004/0015070 A1 | | 1/2004 | Liang et al. | 600/407 |

FOREIGN PATENT DOCUMENTS

WO    2007/133695 A2    11/2007

OTHER PUBLICATIONS

PCT International Search Report and Written Opinion, International App. No. PCT/SUS07/11433, mailed Mar. 5, 2008.

* cited by examiner

*Primary Examiner* — Andrew W Johns
(74) *Attorney, Agent, or Firm* — Michael Best & Friedrich LLP

(57) ABSTRACT

A method of displaying tomographic information. The method comprises defining a compact region within an imaged target and generating an image showing a part of the target encircling the compact region, wherein the compact region represents a bore to be drilled and the generated image shows a perspective view of the wall of the bore from an open end of the bore.

26 Claims, 3 Drawing Sheets

TOMOGRAPHIC IMAGING

BACKGROUND

The invention relates to tomographic imaging, and especially, but not exclusively, to x-ray tomographic dental imaging.

A set of three-dimensional data relating to a property of an object that varies over space within the object may be obtained in various ways. For example, an x-ray image of a target may be obtained by placing the target between a source of x-rays and a detector of the x-rays. In a computed tomography (CT) system, a series of x-ray images of a target are taken with the direction from the source to the detector differently oriented relative to the target. From these images, a three-dimensional representation of the density of x-ray absorbing material in the target may be reconstructed. Other methods of generating a three-dimensional dataset are known, including magnetic resonance imaging, or may be developed hereafter.

Various proposals have been made for displaying the data to a user, such as a doctor or surgeon. The best known display is to provide one or more cross-sectional views of the target in planes parallel to principal axes of the imaging apparatus. However, other display options have been used. For example, in dental work a cross-section in a plane perpendicular to the dental arch has been used.

SUMMARY

According to one embodiment of the invention, there is provided a method and system for displaying tomographic information, in which a compact region within an imaged target is defined, and an image showing a part of the target encircling the compact region is generated.

The compact region may be a part of the imaged target that is proposed to be removed, for example, a proposed drilled bore, and an image is presented showing the target as it would appear after removal of the specified part.

According to a preferred embodiment of the invention, the target is part of the human anatomy, for example, the maxilla or mandible, and the part to be removed is notionally drilled away to form a bore for mounting a surgical prosthesis, for example, a dental implant. The image presented may then be a view of the walls of the bore. Because the drilling and image presentation are virtual, the practical difficulties of inserting a camera into a drilled bore only a few millimeters in diameter may be ignored.

By displaying the walls of the proposed mounting bore, the surgeon is assisted in assessing whether the surrounding bone is sufficiently dense to provide a sound foundation for a dental implant or other prosthesis. Because the bore is virtual, the surgeon can try several different bore positions until he or she finds a satisfactory location for the proposed implant.

In an alternative embodiment, the target is a part of the human anatomy, for example, the maxilla or mandible, in which a surgical prosthesis, for example, a dental implant, has already been installed. The image presented may then show the bone immediately surrounding the implant, assisting the surgeon to assess post-operative osseointegration.

The bone density or other important property of the walls of the bore or other notionally exposed surface may be displayed by color-coding, for example, to indicate bone density categories. It is believed that in some circumstances the color-coding may be easier to read than the shades of gray in which tomograms are commonly displayed.

The invention also provides computer software arranged to generate an image in accordance with the method of the invention, and computer-readable media containing such software. The software maybe written to run on an otherwise conventional computer processing tomographic data.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Reference will now be made in detail to various embodiments of the present invention, examples of which are illustrated in the accompanying drawings.

Figure 1:
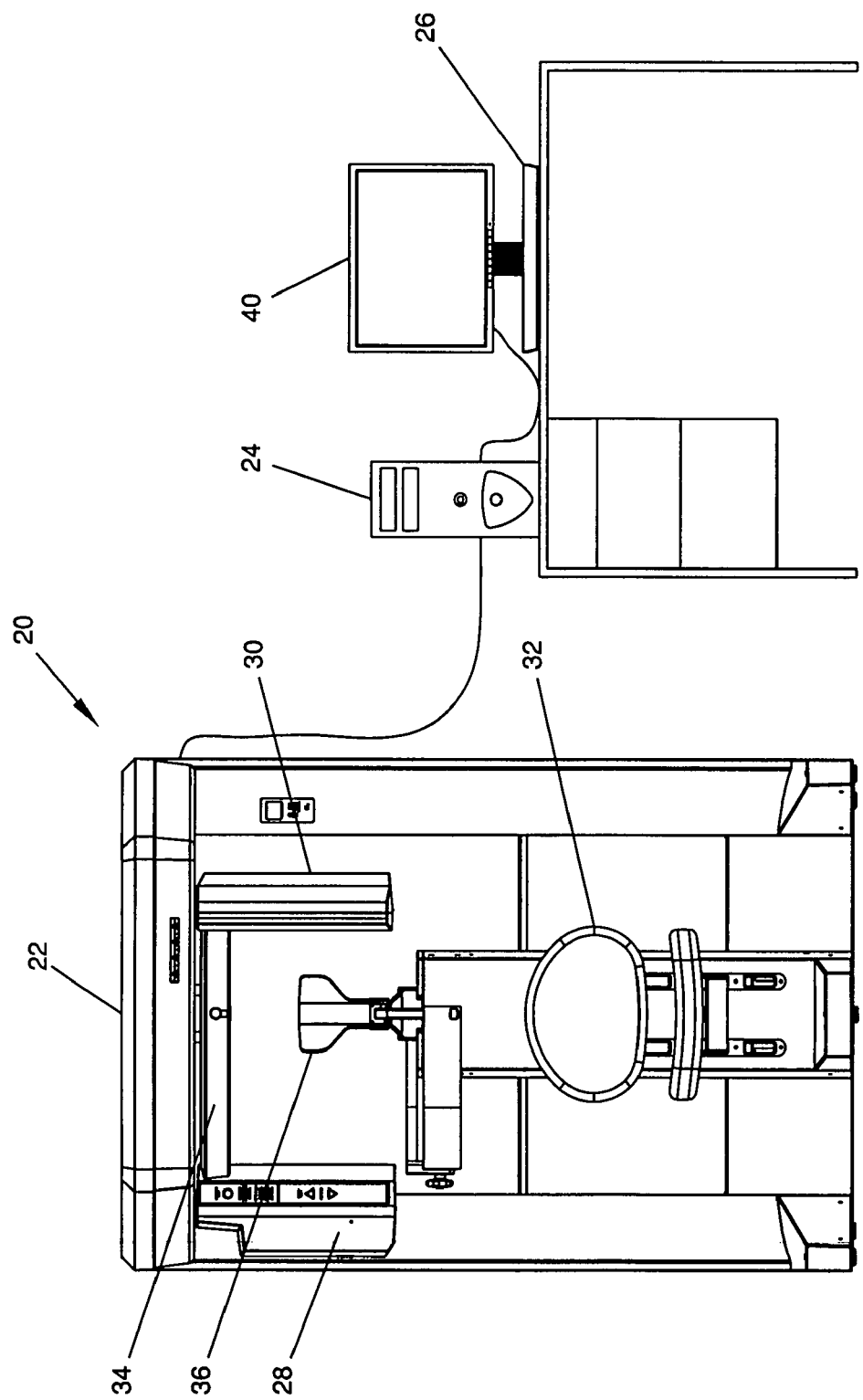
FIG. 1 is a schematic view of apparatus for generating a tomographic image.
Figure 2:
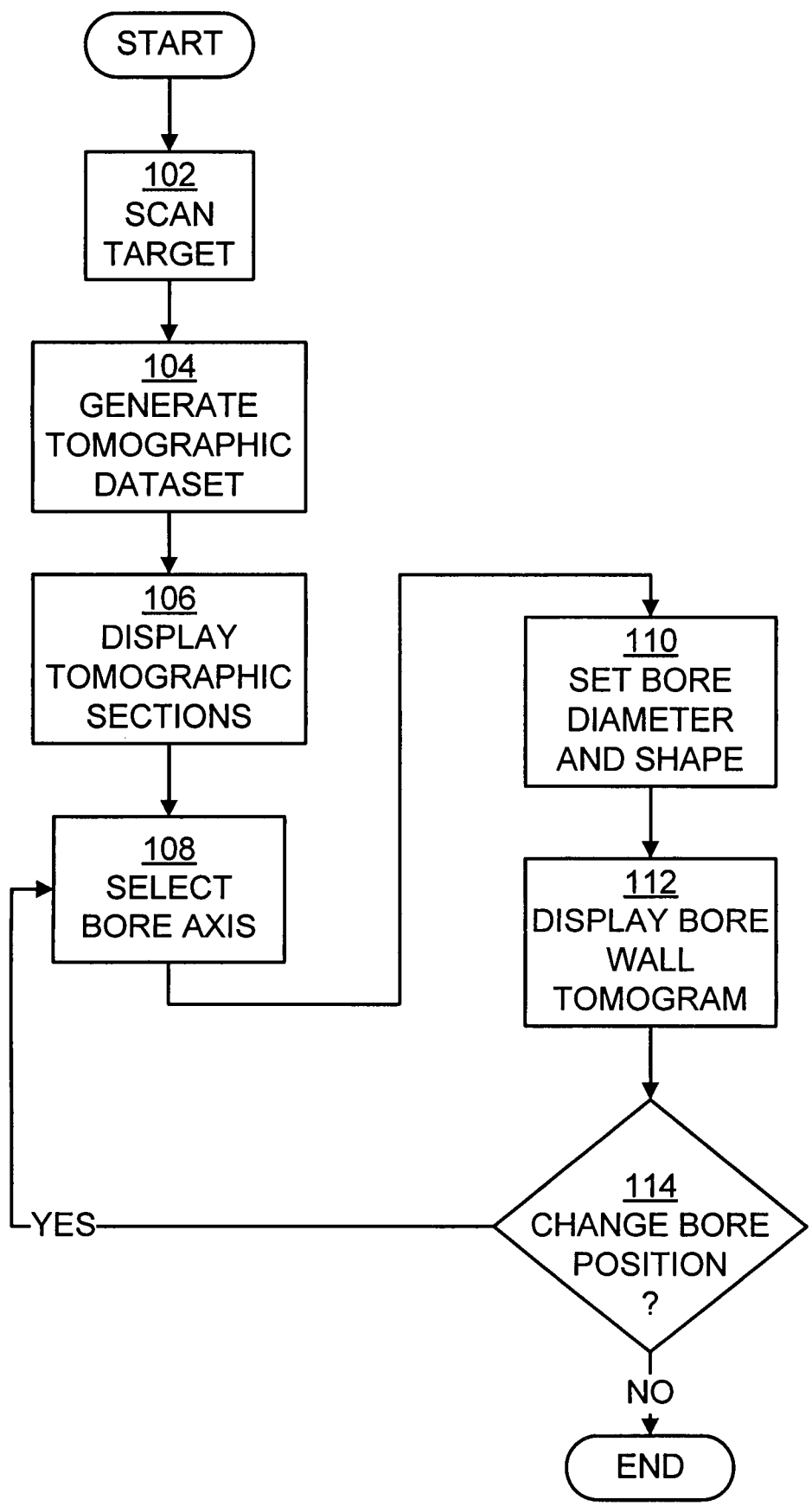
FIG. 2 is a flow chart.

Referring to the drawings, and initially to FIGS. 1 and 2, one form of tomographic apparatus according to an embodiment of the invention, indicated generally by the reference numeral 20, comprises a scanner 22 and a computer 24 controlled by a console 26. The scanner 22 comprises a source of x-rays 28, an x-ray detector 30, and a support 32 for an object to be imaged. In an embodiment, the scanner 22 is arranged to image the head, or part of the head, of a human patient (not shown), especially the jaws and teeth. The support 32 may then be a seat with a rest or restrainer 36 for the head or face (not shown) of the patient. The x-ray source 28 and detector 30 are then mounted on a rotating carrier 34 so as to circle round the position of the patient's head, while remaining aligned with on another. In step 102, the x-ray detector 30 then records a stream of x-ray shadow grams of the patient's head from different angles. The computer 24 receives the x-ray image data from the scanner 22, and in step 104 calculates a 3-dimensional spatial distribution of x-ray density.

The imaging of the patient's head and calculation of the spatial distribution may be carried out by methods and apparatus already known in the art and, in the interests of conciseness, are not further described here. Suitable apparatus is available commercially, for example, the i-CAT Cone Beam 3-D Dental Imaging System from Imaging Sciences International of Hatfield, Pa.

In step 106, existing tomographic imaging systems typically display information on a display 40 of console 26 as a slice or section aligned with the principal axes of the scanning system 22. Dental x-ray systems may also provide sections on a curved surface along the dental arch or in a plane that intersects the dental arch at right angles. Sections may also be taken on planes chosen by the user.

The installation of a dental implant typically involves drilling a bore in the bone of the mandible or maxilla, and inserting a metal post, to an exposed outer end of which a prosthetic tooth is later mounted. The metal post may be, for example, cylindrical or conical, or of a convex shape similar to a cone but with a cone angle that increases towards the tip. Where the post is at least partly cylindrical or only slightly tapered, it may be screw threaded. By inspecting tomographic sections through the intended position of the post, the surgeon can ensure that there will be sufficient thickness of bone around the post. However, the surgeon may wish to assess not only the thickness of the bone available around the proposed implant site, but also the quality of the bone into which the post will be threaded. It is not easy, from flat sections or slices, to gain a clear picture of the bone distribution around the cylindrical surface of a proposed bore. After implantation, the surgeon may wish to assess osseointegration at the implant site. However, metal implants are almost perfectly opaque to x-ray. Consequently, the implant obstructs a direct view of the implant site. In a tomographic view, the metal implant is typically surrounded by a "halo" in which the image is degraded because the implant has obstructed some but not all of the x-ray images from which the tomographic data are synthesized. The surgeon may wish to inspect the implant site with the minimum of obstruction and distraction from the metal implant and the "halo" that forms around the implant.

Therefore, the computer 24 shown in FIG. 1 is programmed to generate a tomographic image in the form of a section on a hollow surface specified by the user of the console 26. In use, the hollow surface typically corresponds to the surface of a proposed bore for the post of an implant. Alternatively, the hollow surface may be taken slightly outside the actual surface of the proposed bore, for example, to show the material that a screw-threaded post will cut into. In step 108, the user may specify the axis of the bore, for example, by positioning one or more conventional tomographic sections along or intersecting the axis, and indicating the position of the axis, or of the point where the axis crosses the sections, with a mouse, touch screen stylus, or other graphical user interface tool. In step 110, the diameter of the bore may be selected from a menu, typed in as a number, or input in another convenient way. Where the bore is not cylindrical, the shape of the bore may be selected from a menu of standard shapes, or may at least in part be entered numerically or graphically. The selected position and size of the bore may be shown superimposed on the tomographic section or sections on the display 40.

Where the tomographic dataset is based on a scan taken after the metal implant is implanted, the hollow surface may surround the implanted post just outside the surface of the metal, or with a small clearance to exclude a volume where the halo is most severe. The computer 24 may be programmed to automatically detect the metal implant and define a bore around it.

In step 110, the computer 24 then generates from the tomographic data a section on the specified hollow surface.

Figure 3:
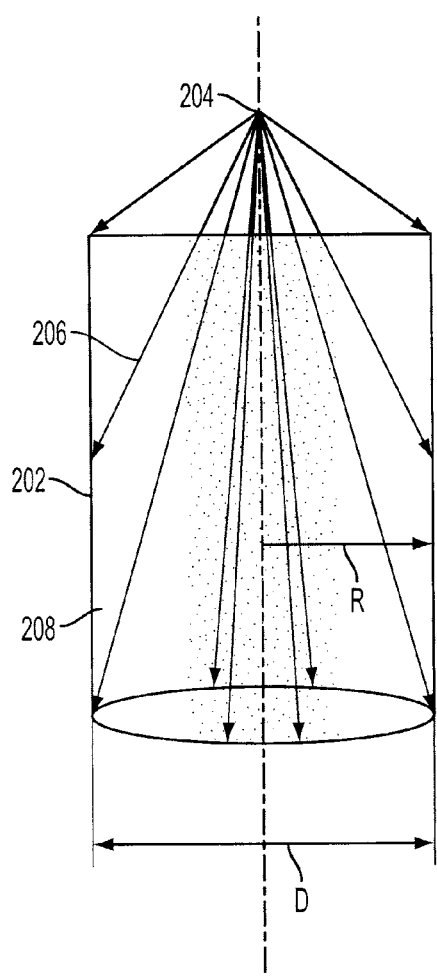
FIG. 3 is a schematic axial section view of a tomographically generated drilled bore.
Figure 4:
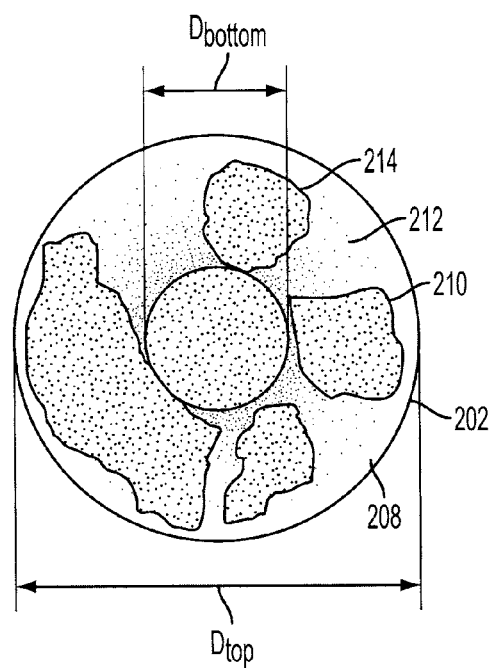
FIG. 4 is a perspective view of a tomographically generated drilled bore from an open end.

Referring now to FIGS. 3 and 4, the section 202 may be displayed as a perspective view from a point 204 just above an open end of the hollow surface. As shown by the arrows 206 in FIG. 3, because of perspective, a cylindrical bore of radius R and diameter D maybe displayed in such a perspective view with the cylindrical side wall 208 of the bore clearly visible. As seen in FIG. 4, the diameter $D_{top}$ of the open end appears larger than the diameter $D_{bottom}$ of the closed end, with the foreshortened side wall 208 occupying an annular area between the top and bottom diameters. If the bore 202 is tapered, then the actual difference between the diameters $D_{top}$ and $D_{bottom}$ combines with the effect of perspective, and increases the annular area representing the side wall. The view of the conical surface in the perspective view is then improved.

Alternatively, the section may be displayed as a three-dimensional view from the concave side, in effect showing the wall of the proposed bore as it would appear to a viewer inside the bore after it has been drilled, although preferably somewhat enlarged. In this case, it is preferred to show half the bore, sectioned down the axis to show a semicircular trough, so that the bore appears on the display 40 as shown in FIG. 3. A control is then provided on the console 26 to enable the plane of section to be rotated round the axis, giving on screen the appearance that the wall of the bore is rotating and allowing the user to view the entire inside of the bore. This is a fairly naturalistic view, because a notional viewer inside the bore would see only about half the wall of the bore at any time, and would turn round to view the whole wall.

Alternatively, both halves of the bore may be displayed side by side, allowing the surgeon to see the whole bore wall at one view.

Alternatively, the entire cylindrical or conical wall could be "developed" or unrolled into a flat image, so that the entire wall can be seen in one view. If the wall has a curvature with a spherical component that is not "developable," it cannot be displayed perfectly as a flat image, but a distorted developed view, like a flat map of the round planet Earth, may still be useful. Many dentists are accustomed to working with a "panoramic" view of the mouth, in which a view, or a tomographic section, of the dental arch (with each part viewed perpendicular to the arch, from either the inside or the outside) is developed into a flat image, and would find such developed images sufficiently familiar to be easily interpreted.

The surgeon is thus able to view the entire surface of the bore into which he or she contemplates inserting the post of an implant, and to determine whether the quality of the bone is sufficient for a securely founded implant. Because the view is prepared tomographically, before any actual surgery has taken place, the surgeon can try alternative sites if he or she decides in step 114 that the originally proposed site is less than satisfactory. Indeed, the surgeon can try any number of alternative sites, which may include overlapping or intersecting sites, until a good site, or the best practical site, is identified. As will be appreciated, that approach would not be practical if an actual bore had to be drilled at each possible site.

When the surgeon positions the virtual implants, the surgeon typically also performs a series of distance and angle measurements. Distance measurements show how close the proposed implant is to some other anatomy, for example to ensure that a minimum distance is maintained to the facial nerve canal. For example, a specific distance may be maintained from a neighboring tooth, or standard distances may be maintained between neighboring teeth, mainly for esthetic reasons, so that the row of teeth including crowns on implants are evenly spaced. The surgeon may also wish to ascertain that a proposed implant does not touch a neighboring tooth root, because that would damage the neighboring tooth. The surgeon typically also performs angular measurements to assess the torque that will be placed on the implant. For example, if an implant is placed into a jaw at 45 degrees to the bite direction and then a crown is placed onto that implant, biting on something hard will put that underlying implant under considerable lateral stress. If osseointegration is not adequate, and the implant placement angle is too large, the implant may break out of its surrounding bone structure. To reduce or avoid that risk, the surgeon aims to keep implant alignment angles to a minimum relative to the bite direction, and angular measurements assist in achieving that goal. To assist in these procedures, the display 40 preferably shows conventional sectional views of the jaw with the proposed implant site marked or superimposed on them, in addition to the views of the notional bore wall surface.

In conventional x-ray tomography, each voxel has a location and a numerical value, typically representing the density or opacity to x-rays of the material occupying that voxel. Tomographic slices or sections are commonly presented on screen with each voxel on the section plane represented by an image pixel, and the opacity of each pixel represented as a shade of gray. For consistency with a traditional film x-ray, the densest material is usually shown with the palest shades. The brightness and contrast can be adjusted for efficient use of the available gray scale. For example, in a tomogram where only bone is of interest, the gray scale may be set so that various bone densities span the gray scale, and soft tissue is all shown as black. In a tomogram where soft tissue structure is important, the gray scale is adjusted to show soft tissue as shades of darker gray, even if the result is that the bone becomes white or a few pale shades and loses detail.

However, even with the gray scale set to give maximum resolution of bone densities, the shades of gray can be difficult to interpret accurately. When assessing the quality of bone for a dental implant, for many purposes a classification into a small number of density types, for example, four density types, each defined as a range of x-ray densities, is sufficient to assess the prospects for a satisfactory implant. The tomographic image may therefore be generated using areas 210, 212, 214 (see FIG. 4) of distinct shades for ranges of density. Although this classification actually reduces the amount of bone density information in the image, the improvement in ease of interpretation may be sufficient to outweigh the loss of information. The implant is placed to achieve, among other factors, a maximum of bone contact for best possible "growing in" or osseointegration, which is ideally achieved by finding solid bone all around the proposed implant location. That is often not obtainable, so the surgeon is searching for a location of maximum bone contact, for which the quick visualization provided by the color-coded display may be of assistance.

Where only a small number of distinct density types is displayed, the types may be shown as areas 210, etc. of distinct colors, instead of shades of gray. The surgeon may then be able to estimate at a glance the proportion of the bore wall that is of each density type, and thus whether there is adequate support for the implant.

Alternatively, or in addition, the computer 24 may be programmed to calculate a quality score for the overall hollow surface, for example by applying rules or formulas based on the percentage of the surface that is of each density type or other category.

Where the quality of the bone is uneven, an average of the bone density over a certain region provides only incomplete data. However, it is presently believed that an image generated from a tomographic dataset with a voxel pitch of 0.4 mm, which is obtainable with the current generation of tomographic dental x-ray machines, is sufficiently fine to provide the surgeon with the information he requires in most cases.

Various modifications and variations can be made in the present invention without departing from the spirit or scope of the invention. Thus, it is intended that the present invention cover modifications and variations of this invention provided they come within the scope of the appended claims and their equivalents.

For example, the computer 24 has been described as generating the cylindrical tomographic image from a generic dataset, which may consist of an array of cubic or cuboidal voxels in an array aligned with the principal axes of the scanner 22. For dental use, a tomographic dataset with the principal axes aligned along and across the dental arch may be preferred. For dental use, the scan may be of limited height, for example, covering only the mandible and/or maxilla, and omitting the upper part of the head. A limited-diameter scan showing only one or a few teeth is sometimes preferred, to reduce x-ray exposure. However, a full-diameter scan showing the entire jaw is presently preferred, because the implant surgeon typically wishes to align the implant relative to the other teeth in both jaws to provide an end result that is esthetically pleasing as well as structurally sound. Once the surgeon has acquired a full dataset of the head, then the surgeon can decide to view only a specific subset of the anatomy or to look at the whole mouth, typically because the surgeon wants to compare the left and right side of the mouth visually for symmetry reasons.

Alternatively, especially where the patient is x-rayed specially for planning of the implant, or where the raw scanner data has been stored and the tomographic dataset can be regenerated specially, the tomographic dataset may be optimized specifically for the specific hollow section. However, specially optimized datasets are seldom sufficiently beneficial to justify the extra effort of generating them, and may be actually disadvantageous if the location originally proposed for the implant proves unsatisfactory and a new section at a different bore location has to be generated.

For example, FIG. 1 shows that the computer 24 on which the process of FIG. 2 is running is connected to the scanner 22. A single computer 24 may both control the scanner 22 and run the process of FIG. 2. Alternatively, part or all of the process of FIG. 2 may be carried out on a separate computer. The data from the scanner 22 may be transferred from computer to computer in a convenient format, for example the DICOM format, at a convenient stage of the process. The data may, for example, be transferred directly from computer to computer or may, for example, be uploaded to and downloaded from a storage server.

For example, although the embodiments have been described as using x-ray tomographic data, another process that provides a suitable array of data about the target, including magnetic resonance tomography and including processes hereafter to be developed, may be used to provide the data from which the processes and apparatus of the present invention generate the desired hollow or perspective view.

What is claimed is:

1. A method of displaying tomographic information, comprising:
    defining a compact region within an imaged target; and
    generating an image showing a part of the target encircling the compact region,
    wherein the compact region represents a bore to be drilled, and the generated image shows a perspective view of a wall of the bore from an open end of the bore.

2. A method according to claim 1, further comprising assessing a quality of a part of the target surrounding the compact region.

3. A method according to claim 2, further comprising, where the quality of the part of the target surrounding the compact region is assessed as unsatisfactory, defining a different compact region within the target, and repeating the generating of an image for the different compact region.

4. A method according to claim 1, further comprising drilling a bore in the target at the location of the defined compact region.

5. A method according to claim 4, where the target is anatomical, further comprising installing a prosthetic implant in the bore.

6. A method according to claim 1, comprising displaying part of the target encircling the compact region as a simulated three-dimensional image.

7. A method according to claim 1, comprising displaying the target encircling the compact region as a developed image.

8. A method according to claim 1, wherein defining the compact region comprises displaying on a graphical user interface a tomographic image of at least one section through the target, and defining on at least one said section a position of an axis of the compact region.

9. A method according to claim 1, further comprising applying to different parts of the image distinct appearances corresponding to categories of a property of the material forming the target.

10. A method according to claim 9, wherein the property is bone density, and the distinct appearances are different colors.

11. A method according to claim 1, further comprising obtaining tomographic data from which to generate the image by scanning the target.

12. A method according to claim 11, wherein scanning the target comprises x-raying the target.

13. A method of displaying tomographic information, comprising:

defining a compact region within an imaged target; and generating an image showing a part of the target encircling the compact region, wherein the compact region represents a bore to be drilled, and the generated image shows a wall of the bore from within the bore.

14. A method according to claim 13, further comprising assessing a quality of a part of the target surrounding the compact region.

15. A method according to claim 14, further comprising, where the quality of the part of the target surrounding the compact region is assessed as unsatisfactory, defining a different compact region within the target, and repeating the generating of an image for the different compact region.

16. A method according to claim 13, further comprising drilling a bore in the target at the location of the defined compact region.

17. A method according to claim 16, where the target is anatomical, further comprising installing a prosthetic implant in the bore.

18. A method of displaying tomographic information, comprising:

defining a compact region within an imaged target; and generating an image showing a part of the target encircling the compact region, wherein the compact region represents a prosthetic component, and the generated image shows the target encircling the prosthetic component, looking away from the prosthetic component.

19. Apparatus for displaying tomographic information, comprising:

a user interface enabling a user to define a compact region of an imaged target; and a processor arranged to generate an image showing a part of the target surrounding the compact region, wherein the processor is arranged to accept the compact region in the shape of a drilled bore, and to generate the image showing a wall of the bore from within the bore.

20. Apparatus according to claim 19, wherein the processor is arranged to display part of the wall of the bore as a simulated three-dimensional image on the user interface.

21. Apparatus according to claim 19, wherein the processor is arranged to display the wall of the bore as a developed image.

22. Apparatus according to claim 19, wherein the user interface is a graphical user interface, on which the processor is arranged to display a tomographic image of at least one section through the target, which is arranged to enable the user to define on at least one said section a position of an axis of the compact region.

23. Apparatus according to claim 19, further comprising a scanner arranged to obtain tomographic data from which to generate the image by scanning the target.

24. Apparatus according to claim 23, wherein scanning the target comprises x-raying the target.

25. A computer program, stored on a non-transitory machine-readable medium, for displaying tomographic information, comprising instructions for:

defining a compact region within an imaged target; and generating an image showing the target as it would appear after removal of the compact region from within the space left by removing the compact region;

wherein the compact region represents a bore to be drilled, and the generated image shows a perspective view of a wall of the bore from an open end of the bore.

26. A non-transitory machine-readable medium storing a computer program according to claim 25.

* * * * *